US006719770B2

(12) United States Patent
Laufer et al.

(10) Patent No.: US 6,719,770 B2
(45) Date of Patent: *Apr. 13, 2004

(54) ULTRASONIC DEVICE FOR PROVIDING REVERSIBLE TISSUE DAMAGE TO HEART MUSCLE

(75) Inventors: Michael D. Laufer, Menlo Park, CA (US); Bruce D. Stambaugh, Anaheim, CA (US); Hien V. Nguyen, Santa Ana, CA (US)

(73) Assignee: Tony R. Brown, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/876,075

(22) Filed: Jun. 8, 2001

(65) Prior Publication Data

US 2001/0025185 A1 Sep. 27, 2001

Related U.S. Application Data

(62) Division of application No. 09/164,420, filed on Sep. 30, 1998, now Pat. No. 6,283,935.

(51) Int. Cl.[7] .............................................. A61B 17/32
(52) U.S. Cl. .......................... 606/169; 604/22; 607/102
(58) Field of Search ............................. 606/32–50, 167, 606/170, 171, 184, 185, 169, 1–14; 604/272, 19–22, 187; 128/898; 607/1, 2, 43, 50, 51, 96, 98–102, 115, 116, 119, 120, 122

(56) References Cited

U.S. PATENT DOCUMENTS

| 3,698,394 A | 10/1972 | Piper et al. |
| 3,794,040 A | 2/1974 | Balamuth |
| 4,654,024 A | 3/1987 | Crittenden et al. |
| 4,658,817 A | 4/1987 | Hardy |
| 5,281,218 A | 1/1994 | Imran |
| 5,314,466 A | 5/1994 | Stern et al. |
| 5,364,393 A | 11/1994 | Auth et al. |

(List continued on next page.)

FOREIGN PATENT DOCUMENTS

WO        00/18305        4/2000

OTHER PUBLICATIONS

Denton A. Cooley, et al. *"Transmycardial Laser Revascularization,"* Texas Heart Institute Journal, vol. 21, No. 3, (1994) pp. 220–224.

Keith A. Horvath et al., *"Transmyocardial Laser Revascularization: Operative Techniques and Clinical Results at Two Years,"* The Journal of Thoracic and Cardiovascular Surgery, (May 1996) pp. 1047–1053.

Keith A. Horvath et al., *"Thoracosopic Transmyocardial Laser Revascularization,"* Ann. Thorac. Surg., vol. 65 (1998).

E. Duco Jansen, et al., *"Laser–Tissue Interaction During Transmyocardial Laser Revascularization,"* Ann. Thorac. Surg. vol. 63, (1997) pp. 640–647.

*Primary Examiner*—Glenn K. Dawson
(74) *Attorney, Agent, or Firm*—Burns Doane Swecker & Mathis, LLP

(57) ABSTRACT

An ultrasonic medical or surgical device creates holes in heart tissue utilizing an ultrasonic needle or probe. The ultrasonic needle is inserted into heart tissue and activated to cause cavitation of fluid surrounding the needle. The cavitation heats the surrounding tissue and causes reversible tissue damage. The ultrasonic device consists of a transducer, a needle, and a regulator. The device can be a hand held device for external application or may be a catheter device for performing a minimally invasive procedure. A temperature sensor may be positioned on the needle for sensing a temperature of the heart tissue in which the needle has been inserted.

20 Claims, 3 Drawing Sheets

U.S. PATENT DOCUMENTS

| | | |
|---|---|---|
| 5,380,316 A | 1/1995 | Aita et al. |
| 5,389,096 A | 2/1995 | Aita et al. |
| 5,397,293 A | 3/1995 | Alliger et al. |
| 5,427,118 A | 6/1995 | Nita et al. |
| 5,533,957 A | 7/1996 | Aldea |
| 5,554,152 A | 9/1996 | Aita et al. |
| 5,607,421 A | 3/1997 | Jeevanandam et al. |
| 5,620,439 A | 4/1997 | Abela et al. |
| 5,716,389 A | 2/1998 | Walinsky et al. |
| 5,722,400 A | 3/1998 | Ockuly et al. |
| 5,769,843 A | 6/1998 | Abela et al. |
| 5,779,699 A | 7/1998 | Lipson |
| 5,873,855 A * | 2/1999 | Eggers et al. ............... 604/114 |
| 5,911,729 A | 6/1999 | Shikhman et al. |
| 5,964,754 A | 10/1999 | Osypka |
| 5,980,545 A * | 11/1999 | Pacala et al. ............... 606/170 |
| 5,980,548 A * | 11/1999 | Evans et al. ............... 606/185 |
| 5,989,274 A * | 11/1999 | Davison et al. ............. 606/169 |
| 6,106,520 A * | 8/2000 | Laufer et al. ................ 606/32 |
| 6,283,935 B1 * | 9/2001 | Laufer et al. ................ 604/22 |
| 6,287,297 B1 * | 9/2001 | Woodruff et al. ............. 606/7 |

\* cited by examiner

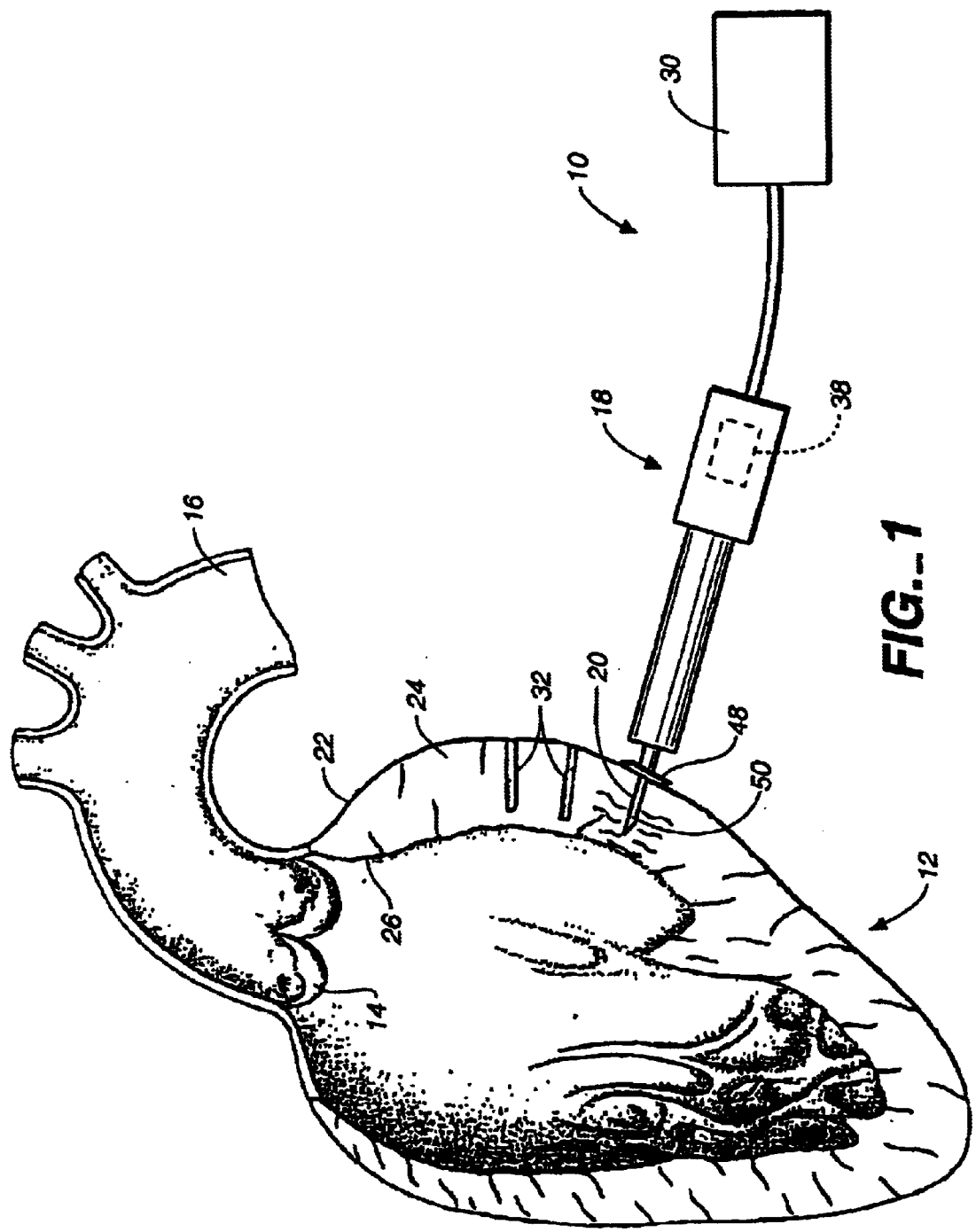
FIG._1

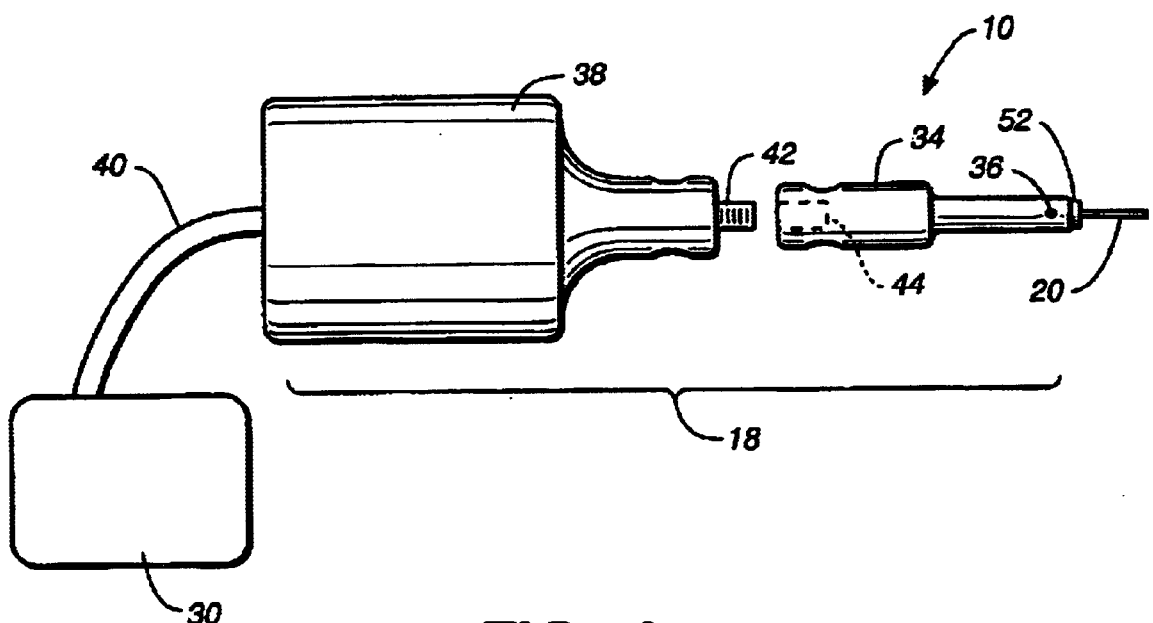
FIG._2
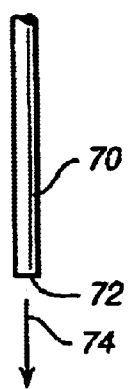
FIG._4
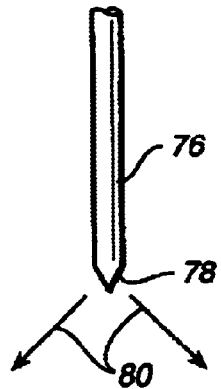
FIG._5

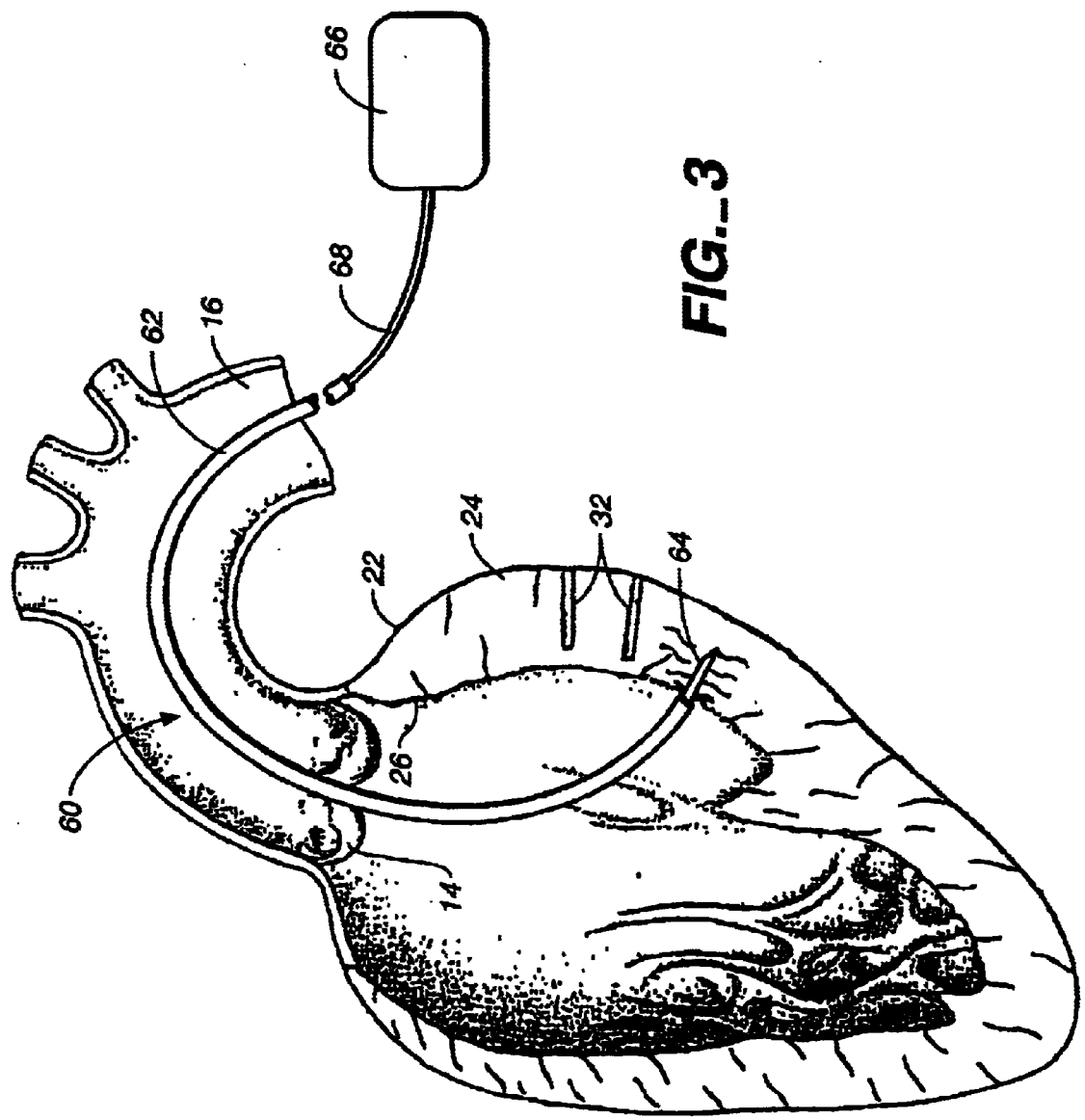
FIG._3

ULTRASONIC DEVICE FOR PROVIDING REVERSIBLE TISSUE DAMAGE TO HEART MUSCLE

This application is a divisional of application Ser. No. 09/164,420, filed on Sep. 30. 1998, now U.S. Pat. No. 6,283,935.

BACKGROUND OF THE INVENTION

1. Field of the Invention

The invention relates to a medical/surgical device and method for treating the heart, and more particularly, the invention relates to an ultrasonic device and method for creating holes in heart tissue.

2. Brief Description of the Related Art

Currently there are a number of companies using lasers to create holes in heart tissue, for example, Cardiogenesis Corporation of Sunnyvale, Calif.; PLC Systems, Inc. of Franklin, Mass.; and Eclipse Surgical Technologies, Inc. of Palo Alto, Calif. Each of these companies are utilizing lasers as an energy source to vaporize heart tissue to create a plurality of holes in the heart for treating angina and heart ischemia.

Angina is sever cardiac pain most often due to ischemia of the myocardium. Ischemia is localized tissue anemia due to a partial or temporary obstruction of inflow of arterial blood. Ischemic tissue in the heart is usually found in the left ventricle due to a partial or temporary obstruction or constriction of the coronary arteries. The procedure of forming holes in the myocardial tissue of the heart is referred to as transmyocardial revascularization ("TMR"). The purpose of TMR is to improve blood flow to under perfused myocardium. The laser created TMR holes are generally formed in the left ventricle. The holes are typically 1 mm in diameter and are placed on a 1 cm by 1 cm grid. Depending on the extent of the angina and ischemia, the laser is used to make somewhere between 10 and 50 holes. Once the holes are created, the holes are sealed off at an exterior of the heart using pressure on the epicardial surface to prevent bleeding into the pericardium.

Studies of TMR procedures on humans have had encouraging results. For example, studies have found a two class reduction in angina in some patients following TMR surgery. This two class reduction of angina greatly increases the quality of life for patients suffering from classes III and IV angina. Patients having classes III and IV angina may not be able to carry on daily activities such as walking without sever pain and may be frequently hospitalized due to heart pain. Following TMR surgery some class III and IV angina patients experience minimal or no angina for up to two years following surgery. Although these studies show that the TMR procedure improved the patients condition and quality of life, it is not yet clear how the formation of holes in the myocardium provides this marked improvement in patient condition.

Three hypophysis for the improvement which has been observed are that 1) blood flow through the TMR channels directly perfuses the myocardium, 2) damage to heart tissue from ablation and heat of the laser causes release of growth factors that result in angiogenesis, and 3) destruction of nerve pathways mask angina and prevents pain. Because the positive results of TMR surgery last up to two years, and the channels have closed by this time, it is believed that direct tissue perfusion is not the sole reason for the observed improvement.

Currently TMR is being performed utilizing a laser source of energy which forms a hole all the way through the heart tissue. Once the holes are formed by the laser, the surgeon, must cover the hole by placing a finger on the epicardial surface until the hole clots shut or the surgeon may use a suture to close the hole. Another disadvantage of the use of a laser is the cost. The laser energy source for use in this procedure costs between about $200,000 to $700,000. This creates a high cost of performing the TMR procedure. Additionally, the laser TMR procedure vaporizes viable heart tissue.

Accordingly, it would be desirable to provide a cost effective supply of energy to create holes in heart tissue. It is also preferable that the energy delivery system does not vaporize viable heart tissue, and does not form holes all the way through the heart tissue.

SUMMARY OF THE INVENTION

The present invention relates to a device that creates holes in heart tissue utilizing ultrasonic energy. The device consists of an ultrasonic generator, a regulator, and an ultrasonic needle for delivering ultrasonic energy to the heart tissue. The ultrasonic device is significantly less expensive than the laser device. In addition, the ultrasonic device does not vaporize heart tissue but instead creates a zone of reversible tissue damage caused by the heating of the tissue. Thus, the present invention provides a significant advance over the current laser TMR therapy.

In accordance with one aspect of the present invention, an ultrasonic device for treating ischemia and angina includes a needle, an ultrasonic transducer for delivering ultrasonic energy to the needle, and a temperature sensor positioned on the needle for sensing the temperature of heart tissue in which the needle has been inserted.

In accordance with an additional aspect of the present invention, a method of performing transmyocardial revascularization includes inserting a needle into heart tissue, and applying ultrasonic energy to the needle for a period of time sufficient to create a zone of reversible tissue damage surrounding the needle.

In accordance with a further aspect of the invention, a method of treating ischemia and angina by causing reversible damage to myocardial tissue includes inserting a needle into the myocardial tissue, applying ultrasonic energy to the needle, and heating the myocardial tissue to between about 40° C. and about 60° C. to create a zone of reversible tissue damage around the needle.

The ultrasonic energy may be applied by inserting the needle from an exterior of the heart or may be applied minimally invasively with a needle at the end of a catheter.

The present invention provides advantages of a TMR device which does not vaporize viable heart tissue or create holes al the way through the heart tissue.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a cross sectional view of a left ventricle of a heart with an ultrasonic device for creating holes in the heart tissue;

FIG. 2 is a side view of an ultrasonic device for creating holes in heart tissue;

FIG. 3 is a cross sectional view of a left ventricle of a heart with a minimally invasive ultrasonic device for creating holes in the heart tissue;

FIG. 4 is a side view of a needle for use in the present invention; and

FIG. 5 is a side view of an alternate needle for use in the present invention.

DETAILED DESCRIPTION OF THE PREFERRED EMBODIMENTS

The present invention provides a device and method for transmyocardial revascularization ("TMR") utilizing an ultrasonic device 10 for heating heart tissue. FIG. 1 is a schematic illustration of the ultrasonic device 10 according to one embodiment of the present invention with a needle 20 inserted into left ventricular tissue of the heart. The left ventricle is illustrated in cross-section with the mitral valve (the valve controlling blood flow from the left atrium to the left ventricle) not illustrated. The left ventricle wall 12 is primarily composed of heart muscle tissue. When the muscle tissue contracts, blood is expelled from the ventricle through the aortic valve 14, and into the aorta 16 for delivery blood to the body. When the myocardium or muscle tissue is under perfused, it cannot successfully achieve the function of delivering blood to the body.

The ultrasonic device 10 for creating holes includes a handle 18 containing an ultrasonic generator or transducer 38 and a needle 20 attached at the distal end of the handle. The needle 20 is introduced into the tissue of the left ventricle starting on the epicardial surface 22 and penetrating the myocardial tissue 24. The needle 20 preferably does not penetrate the endocardial surface 26. After or during insertion of the needle 20 into the tissue 24 the ultrasonic transducer 38 of the device 10 is activated to vibrate the needle longitudinally.

The ultrasonic vibrations of the needle 20 create millions of microscopic bubbles or cavities in fluid, e.g. water, adjacent the needle. The bubbles expand due to the creation of a negative pressure when the needle 20 moves away from the tissue during a vibration. The bubbles implode violently as the needle moves into the tissue during a vibration. This phenomenon, referred to as cavitation, produces a powerful shearing action at the needle tip and causes the cells in the tissue to become disrupted. This disruption causes small blood vessels such as capillaries and arterioles to disrupt and form a reversible hematoma (bruise) type injury to the heart.

The heating of the myocardial tissue 24 by application of ultrasonic energy creates a zone of reversible tissue damage surrounding the needle 20. In accordance with the present invention, the volume of the zone of reversible tissue damage is preferably maximized while the volume of permanent tissue damage is minimized. The reversible tissue damage area acts like a bruise and causes angiogenesis (creation of capillaries and arteries) and arteriogenesis (creation of small arteries). The newly created blood vessels resulting from the ultrasonic treatment improve tissue perfusion and relieve chronic ischemia and angina.

As illustrated in FIG. 1, preferably the needle 20 is inserted into the myocardial tissue 24 so that it does not puncture the endocardial surface 26. When ultrasonic energy is applied to the needle 20, the zone of reversible tissue damage created around the needle extends radially from the needle and axially from the tip of the needle. Accordingly, the zone of reversible tissue damage will preferably extend all the way through to the endocardial surface 26. Although FIG. 1 illustrates visible holes 32 formed though the myocardial tissue 24, in fact, once the needle 20 has been withdrawn the holes formed by the needle 20 will be very small or even imperceptible.

FIG. 2 illustrates one embodiment of the ultrasonic device 10 in which the needle 20 is removably attached to the handle 18 and secured in the handle with a set screw 36 or other securing device. The handle 18 preferably includes a metal probe 34 and a transducer 38. The metal probe 34 transmits ultrasonic energy from the transducer 38 to the needle 20. The probe 34 may be an aluminum probe having a length of about 0.5 to 5 inches, preferably about 1.4 inches. The probe 34 preferably has a first larger diameter section for connection to the transducer 38 and a second smaller diameter section for receiving the needle 20.

The transducer 38 may be any known ultrasonic transducer which provides ultrasonic vibration along a single axis. For example, the transducer 38 may include a piezoelectric crystal which vibrates in the ultrasonic range upon application of an electric voltage. The transducer 38 includes a horn 42 which is received within a proximal end of the probe 34. The horn 42 is received in a corresponding blind hole 44 in the probe 34. The transducer 38 causes vibration of the needle 20 substantially along an axis of the needle with minimal vibration in other directions.

The transducer 38 is connected by an electrical cable 40 to the regulator 30 which controls the ultrasonic device 10. The needle 20 is optionally provided with a standard thermocouple 50 welded within the lumen of the needle or on an exterior of the needle. The thermocouple 50 is preferably located about 5 mm from the distal tip of the needle 20. The thermocouple 50 is used to give the operator of the device an indication of the temperature of the needle 20 and thus, the temperature of the adjacent heart tissue. The thermocouple 50 may be any known thermocouple, such as a thermocouple formed of a chrome alumel and constantan wire.

According to one preferred embodiment of the invention, lead wires are provided to connect the thermocouple to the regulator 30 for control of heating. The regulator 30 may control the temperature of the heart tissue in which the needle 20 has been inserted by controlling the application of ultrasonic energy. Since the probe 34 will tend to heat up during operation, preferably a cooling pad 52, illustrated in FIG. 2, is positioned around a distal end of the needle 20 between the probe 34 and the tissue. The regulator 30 can be used to ensure that frictional energy does not heat the heat tissue to a temperature that will permanently damage the tissue. It is currently desirable to maintain the heart tissue between 37° C. and 60° C., more preferably between 37° C. and 50° C.

The needle 20 may be made out of a rigid material such as stainless steel or titanium. The diameter of the needle 20 can vary, however the preferred diameters range from about 0.1 mm to about 3 mm with 1 mm being presently preferred. The length of the needle can also vary to match the left ventricular wall thickness. The needle length is preferably slightly less than a thickness of the myocardial tissue 24. Preferably, the needle 20 extends about 80–90% of the way through the heart tissue. For example, for tissue about 20 mm thick, a 16–18 mm needle, and preferably a 17 mm needle will be used.

The very distal end of the needle 20 is beveled to provide a sharp point for penetrating the heart tissue. The needle 20 can be fixed to the distal end of the probe 34, or can be removably attached to the probe with the set screw 36 as shown.

The transducer 38 operates at a frequency in the ultrasonic range, 1 to 100 kHz, preferably the transducer operates at 20 kHz or 40 kHz. The transducer 38 may operate at 5 to 200 watts, preferably between about 20 and 50 watts. The ultrasonic device 10 can measure the temperature at the thermocouple 50 inside or outside the needle to regulate the application of ultrasonic energy by turning the transducer on and off to maintain a set temperature or temperature range. Presently, a temperature ranging from about 37° C. to about 60° C. is used with a temperature of 37° C. to 50° C. being presently preferred. The ultrasonic energy can be delivered for a set time ranging from 1 second to 500 seconds, with 30 seconds being presently preferred.

As shown in FIG. 1, at a distal end of the handle 18 is a soft disk shape stop member 48. The stop member 48 may be used to limit the penetration of the needle 20 into the heart tissue. The stop member 48 is preferably formed of a soft flexible material such as rubber which will assist the surgeon in holding the needle 20 in place in the heart tissue at the desired depth particularly during beating heart surgery. The stop member 48 may be secured to the needle 20 or to the handle 18 such as by epoxy. Alternatively, the stop member 48 may be held in place by a friction fit.

According to one preferred embodiment of the invention, the ultrasonic device 10 is a disposable battery powered device including a battery compartment within the handle 18 in place of the electric cable 40. The regulator 30 may also be incorporated within the handle 18 of the device.

In use of the embodiment of FIGS. 1 and 2, the needle 20 is inserted into the heart tissue by a health care practitioner, preferably a physician, under a procedure that exposes the heart. The needle is placed such that the needle's distal tip does not penetrate the endocardial surface 26 as shown in FIG. 1. A stop 48 as shown in FIG. 1 may be used to limit the penetration depth of the needle 20. In addition, to ensure that the needle 20 does not puncture the endocardial surface 26, appropriate feedback mechanisms can be used such as echocardiography, electrograms, fluoroscopy, and the like. Ultrasonic energy is then applied to the needle 20 by the transducer 38 causing cavitation of fluid and heating the tissue surrounding the needle to cause reversible tissue damage. The regulator 30 controls the temperature of the heart tissue to a temperature of about 40° C. to about 60° C., and preferably about 44 to about 50° C. as sensed by the thermocouple 50. Heating is continued for between about 5 and 120 seconds, preferably about 30 seconds. The needle 20 is then removed and the procedure is repeated as needed to generate an appropriate number of holes 32 depending on the patients condition. The resulting holes 32 are surrounded by a relatively large area of reversible tissue damage which causes increased angiogenesis and/or arteriogenesis. Over time, the ischemic area of the heart which has been treated by the ultrasonic device 10 becomes better perfused with blood and the patient with angina experiences less pain.

FIGS. 4 and 5 illustrate different needle configurations for different cavitation effects. The needle 70 in FIG. 4 has a blunt tip 72 with a 90 degree angle from the axis of the needle. This blunt tip generates cavitation forces 74 axially distal to the blunt tip. The needle 76 in FIG. 5 has a sharp tip 78 with a 45° angle from the axis of the needle. This generates cavitation forces 80 that spread away from the needle at angles of 45° with respect to the needle axis. Varying the angle of the tip of the needle controls the direction of the cavitation forces. Currently angles varying from about 5° to about 90° are used with angles of 30, 45 and 60 degrees being presently preferred.

A minimally invasive embodiment of the present invention is illustrated in FIG. 3. The ultrasonic device 60 of FIG. 3 includes a catheter 62 which is fed from an access site such as the femoral artery through the vasculature into the aorta 16 and through the aortic valve 14 into the left ventricle of the heart. An ultrasonic needle 64 is positioned within the catheter. The ultrasonic needle 64 is deployed from the catheter and inserted through the endocardial surface into the myocardial tissue 24. Ultrasonic energy is delivered to the needle 64 from an ultrasonic transducer 66 which is positioned outside of the body at a proximal end of the catheter 62. The ultrasonic energy is transmitted through the catheter 62 by a flexible shaft 68 to the needle 64. Alternatively, the ultrasonic transducer may be provided within the catheter.

The catheter 62 is preferably constructed out of standard catheter materials such as polyurethane, polyimide, and the like. Typically, the catheter 62 will be extruded via well known means in the art. The catheter 62 will have at least one lumen for delivery of the ultrasonic energy from the transducer 66 to the needle 64. Multiple lumens may also be provided for drug delivery, visualization, and the like. The length of the catheter 62 is such that it is long enough to place the distal end of the catheter having the needle 64 within the heart from a remote access site such as a femoral artery. A typical catheter for access from a femoral artery is 80 cm to 140 cm long. The diameter of the catheter 62 may vary with smaller diameters being preferred. The catheter diameters may range from about 3 French to about 10 French.

The elongated shaft 68 is used to both deliver the ultrasonic energy to the needle and to move the needle between an extended and a retracted position when the catheter has been positioned within the heart.

The minimally invasive ultrasonic device 60 illustrated in FIG. 3 operates in substantially the same manner as described above with respect to FIGS. 1 and 2. The length of the needle 64 is preferably selected such that the needle does not penetrate all the way through to the epicardial surface 22 of the heart. This prevents bleeding into the pericardium.

According to an alternative embodiment of the present invention, the application of ultrasonic energy can be coupled with another form of heating such as resistance heating to heat the surrounding heart tissue. Presently, resistive heating of the heart tissue to between 40° C. and 60° C. and preferably between 44° C. and 50° C. is used.

According to another embodiment of the present invention, the lumen of the needle 20 can be used to deliver beneficial agents to the heart tissue during or after the TMR procedure. For example, a syringe may be attached to a lure fitting of the ultrasonic device for delivery growth factors into the hole formed by the needle. Examples of growth factors include vascular endothelial growth factor (VEGF), fibroblast growth factor (FGF), monocyte attracting protein (MAP), and the like.

The method and apparatus according to the present invention provide several advantages over the prior art TMR methods employing lasers. In particular, the known laser procedure punctures the heart tissue all the way through allowing bleeding into the pericardium and requiring the additional step of application of pressure to cause clotting or stitching the holes close. The present invention achieves the benefits of laser TMR without puncturing all the way through the heart tissue. In addition, the present invention causes less permanent damage to the heart tissue because it does not remove or vaporize tissue. Because tissue is not removed, possible overlapping of holes does not create the same problems in the present invention as in laser TMR procedures. Finally, the TMR procedure according to the present invention employing ultrasonic energy is much less expensive than laser TMR.

While the invention has been described in detail with reference to the preferred embodiments thereof, it will be apparent to one skilled in the art that various changes and modifications can be made and equivalents employed, without departing the present invention.

What is claimed is:

1. A method of performing transmyocardial revascularization comprising:
   inserting a needle into heart tissue;
   applying ultrasonic energy to the needle for a period of time sufficient to create a zone of reversible tissue damage surrounding the needle; and
   controlling the amount of ultrasonic energy applied to the needle based on a measurement of the temperature of the heart tissue contacting the needle to heat the tissue contacting the needle to a temperature of about 37° C. to about 60° C.

2. The method of claim 1, wherein the needle is inserted into the heart tissue from an exterior of the heart.

3. The method of claim 1, wherein the needle is inserted into the heart tissue from an interior of the heart by use of a catheter device.

4. The method of claim 1, wherein the needle is inserted into the heart tissue without penetrating all the way through a wall of the heart.

5. The method of claim 1, wherein the needle is inserted and ultrasonic energy is applied at a plurality of locations to create a plurality of zones of reversible tissue damage.

6. The method of claim 1, wherein the application of ultrasonic energy to the needle heats tissue surrounding the needle to a temperature of about 40° C. to about 60° C.

7. The method of claim 1, wherein the ultrasonic energy is applied at a frequency of about 1 to 100 kHz.

8. A method of treating ischemia and angina by causing reversible damage to myocardial tissue, the method comprising:
   inserting a needle into the myocardial tissue;
   applying ultrasonic energy to the needle; and
   controlling the amount of ultrasonic energy applied to the needle to heat the myocardial tissue contacting the needle to between about 40° C. and about 60° C. to create a zone of reversible tissue damage around the needle.

9. The method of claim 8, wherein the ultrasonic energy is applied at a frequency of about 20 to 40 kHz.

10. The method of claim 8, wherein the needle is inserted into the endocardial and myocardial tissue and does not puncture the epicardial tissue.

11. A method of treating ischemia and angina by causing reversible damage to myocardial tissue, the method comprising:
    inserting a needle into the myocardial tissue wherein the needle is inserted into the epicardial and myocardial tissue and does not puncture the endocardial tissue;
    applying ultrasonic energy to the needle; and
    heating the myocardial tissue to between about 40° C. and about 60° C. to create a zone of reversible tissue damage around the needle.

12. A method of performing transmyocardial revascularization comprising:
    inserting a needle into heart tissue, the needle including a solid distal tip;
    applying ultrasonic energy to the needle for a period of time sufficient to create a zone of reversible tissue damage surrounding the needle; and
    controlling the amount of ultrasonic energy applied to the needle based on a measurement of the temperature of the heart tissue contacting the needle to heat the tissue contacting the needle to a temperature of about 37° C. to about 60° C.

13. A method for treatment of tissue comprising:
    inserting a needle into the tissue;
    applying ultrasonic energy to the needle for a period of time sufficient to create a zone of reversible tissue damage surrounding the needle; and
    controlling the amount of ultrasonic energy applied to the needle based on a measurement of the temperature of the tissue contacting the needle to heat the tissue contacting the needle to a temperature of about 37° C. to about 60° C.

14. The method of claim 13, wherein the tissue is heart tissue.

15. The method of claim 14, wherein the needle is inserted into the heart tissue from an exterior of the heart.

16. The method of claim 14, wherein the needle is inserted into the heart tissue from an interior of the heart by use of a catheter device.

17. The method of claim 14, wherein the needle is inserted into the heart tissue without penetrating all the way through a wall of the heart.

18. The method of claim 13, wherein the needle is inserted and ultrasonic energy is applied at a plurality of locations to create a plurality of zones of reversible tissue damage.

19. The method of claim 13, wherein the application of ultrasonic energy to the needle heats tissue surrounding the needle to a temperature of about 40° C. to about 60° C.

20. The method of claim 13, wherein the ultrasonic energy is applied at a frequency of about 1 to 100 kHz.

* * * * *